United States Patent [19]

Uitti

[11] 4,009,217
[45] Feb. 22, 1977

[54] PROCESS FOR PRODUCTION AND DEHYDROGENATION OF ETHYLBENZENE

[75] Inventor: Kenneth D. Uitti, Bensenville, Ill.

[73] Assignee: Universal Oil Products Company, Des Plaines, Ill.

[22] Filed: May 6, 1975

[21] Appl. No.: 574,985

[52] U.S. Cl. .................. 260/669 R; 260/671 R
[51] Int. Cl.² .................. C07C 15/00; C07C 15/10
[58] Field of Search ........ 260/669 R, 671 C, 671 R

[56] References Cited

UNITED STATES PATENTS

| | | | |
|---|---|---|---|
| 2,851,502 | 9/1958 | Bowman et al. | 260/669 R |
| 2,939,890 | 6/1960 | Hervert et al. | 260/669 R |
| 3,000,986 | 9/1961 | Olan et al. | 260/671 R |
| 3,294,856 | 12/1966 | Huckins | 260/669 R |
| 3,492,222 | 1/1970 | Van Tassell | 208/321 |
| 3,515,765 | 6/1970 | Berger | 260/669 R |
| 3,515,766 | 6/1970 | Root et al. | 260/669 R |
| 3,525,776 | 8/1970 | Berger | 260/669 R |
| 3,847,968 | 11/1974 | Hughes | 260/669 R |
| 3,894,090 | 7/1975 | Cleveland | 260/671 C |
| 3,917,733 | 11/1975 | Winter | 260/671 R |

FOREIGN PATENTS OR APPLICATIONS

| | | | |
|---|---|---|---|
| 1,301,874 | 1/1973 | United Kingdom | 260/669 R |

OTHER PUBLICATIONS

Handbook of Chem. & Phy.–55th Ed.–p. C474.
Condensed Chemical Dictionary–p. 673–8th Ed.–(Hawley–Ed.).

*Primary Examiner*—Oscar R. Vertiz
*Assistant Examiner*—Eugene T. Wheelock
*Attorney, Agent, or Firm*—James R. Hoatson, Jr.; Robert W. Erickson; William H. Page, II

[57] ABSTRACT

Ethylbenzene is produced by the alkylation of benzene and subsequently catalytically dehydrogenated to produce styrene in a process wherein a benzene sidecut stream removed from the fractionation zone separating the newly produced ethylbenzene is water washed to remove a boron-containing complex. The washed sidecut stream is then utilized as the solvent stream fed to a liquid-liquid extraction zone which treats a water stream formed by condensing the effluent of a dehydrogenation zone. The treated water stream is used to generate steam and the extract stream removed from the extraction zone is combined with the effluent of the dehydrogenation zone to cool and dilute the effluent and to recover styrene and ethylbenzene.

4 Claims, 1 Drawing Figure

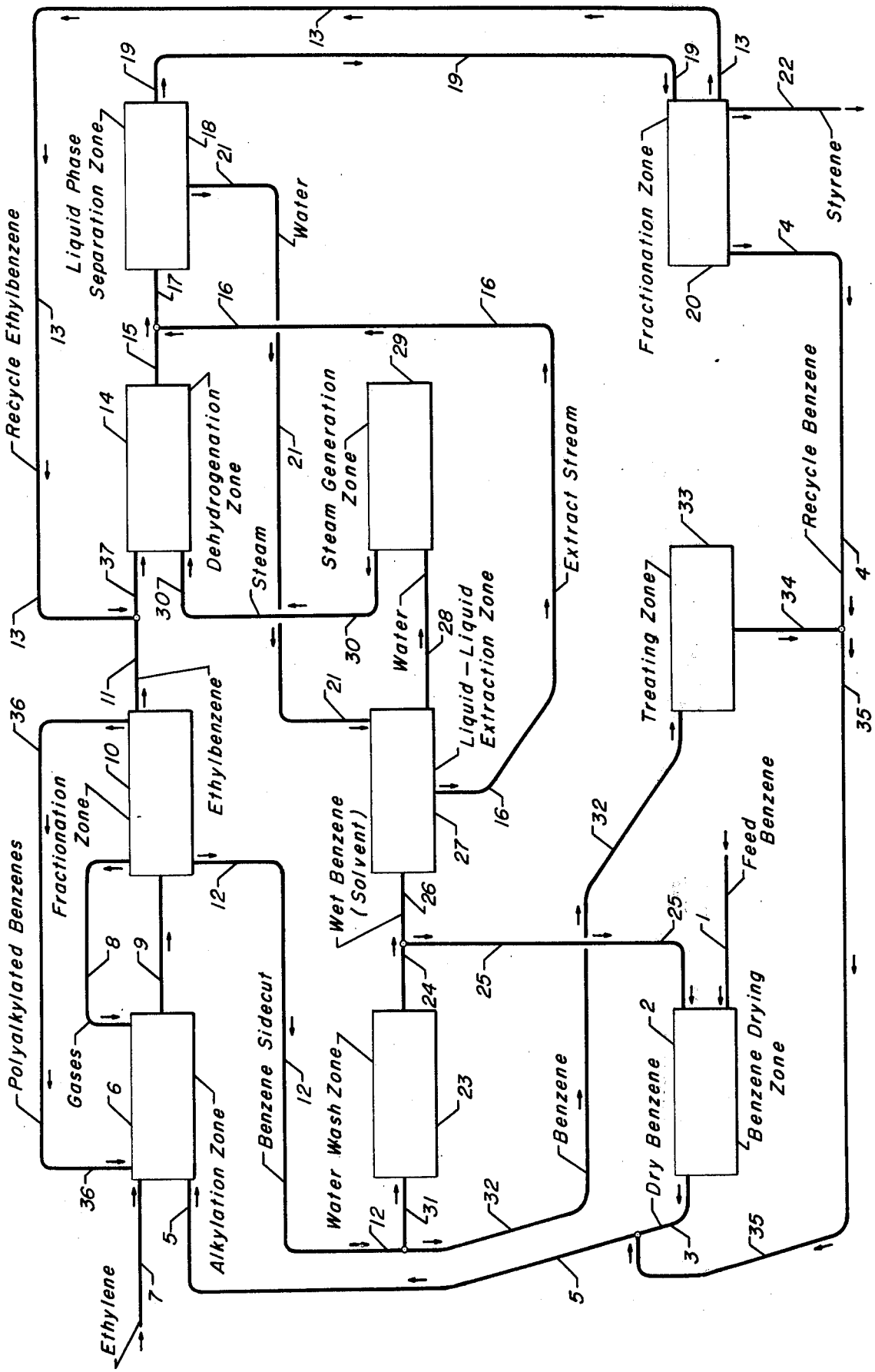

PROCESS FOR PRODUCTION AND DEHYDROGENATION OF ETHYLBENZENE

FIELD OF THE INVENTION

The invention relates to a combination process for the production of styrene by the alkylation of benzene to produce ethylbenzene and the subsequent catalytic dehydrogenation of the ethylbenzene. The invention more specifically relates to such a process wherein styrene and ethylbenzene are removed from water condensed out of the dehydrogenation zone effluent by solvent extraction and wherein a benzene recycle stream is treated for the removal of a volatile borate complex before it is returned to an alkylation zone.

DESCRIPTION OF THE PRIOR ART

Processes for the alkylation of benzene with ethylene to produce ethylbenzene are well known to those skilled in the art. For instance, a process using a boron trifluoride-promoted catalyst is described in U.S. Pat. No. 3,126,421 (Cl. 260–671). This process is troubled by the formation of insoluble boron oxide hydrates from water which enters the reaction zones. To prevent the deposition of these materials in the process vessels, a relatively pure boron halide stream is passed into the lower portion of the distillation column to which the hydrate containing reactor effluent stream is charged. The halide forms a volatile complex with the boron oxide hydrate. This hydrate-containing complex then leaves the distillation column dissolved in a benzene recycle stream removed as a sidecut, and the benzene recycle stream is passed through beds of alumina, which selectively absorb the complex. The benzene recycle stream is then returned to the reaction zones.

The art of alkylaromatic hydrocarbon dehydrogenation is also well developed as shown by the many commercial plants in operation and the wealth of literature in the field. Exemplary processes are shown in U.S. Pat. Nos. 3,515,765 and 3,515,766 (Cl. 260–669). Both of these references teach a process for the catalytic dehydrogenation of an alkylaromatic hydrocarbon, such as ethylbenzene, in which steam is passed through a reaction zone in admixture with the alkylaromatic hydrocarbon. The effluent of the reaction zone is cooled sufficiently to cause condensation of the water and heavier hydrocarbons. The effluent is then passed into a separator, and a water phase is removed and passed into a water stripper for the removal of hydrocarbons.

In the former reference, the water purified in the stripper is heat-exchanged with the reaction zone effluent to form steam used for stripping in a fractionation column. The steam is removed as an overhead vapor containing undehydrogenated hydrocarbons and returned to the reaction zone. In the latter reference, the stripped water is passed through a filter to remove hydrocarbons not removed in the stripper. It is recognized that the 0.01 to 0.08 mole percent of non-aromatic hydrocarbons in solution and in suspension will eventually foul heat-exchangers and boilers used to generate steam. The use of the filter therefore facilitates the passage of the stripped water into a fired feed heater.

U.S. Pat. No. 3,525,776 describes an integrated process for the manufacture and dehydrogenation of ethylbenzene through the use of alkylation, dehydrogenation and fractionation zones similar to that employed in the present invention.

U.S. Pat. No. 3,492,222 (Cl. 208–321) presents a solvent recovery method for use in a liquid-liquid extraction process. Non-aromatic hydrocarbons are removed from an aqueous wash stream by contacting the wash stream with an aromatic hydrocarbon. This is performed to avoid contamination of an aromatic extract by the non-aromatic hydrocarbond when this water is utilized to form the stripping steam used in separating the aromatic extract from a rich solvent.

SUMMARY OF THE INVENTION

The invention provides a combination process for the production and dehydrogenation of ethylbenzene wherein, (1) a boron-containing complex is removed from a benzene recycle stream of the alkylation section by water washing the stream, (2) the water washed benzene is then used as the solvent fed to a liquid-liquid extraction zone which removes styrene and ethylbenzene from a recycle water stream of the dehydrogenation section, and (3) the styrene and ethylbenzene are then recovered by admixing the extract stream of the extraction zone with the effluent stream of the dehydrogenation zone.

DESCRIPTION OF DRAWING

The drawing illustrates the interconnection of the different zones used in practice of several embodiments of the invention.

A high purity benzene feed stream entering the process through line 1 is passed into a benzene drying zone 2. A stream of dry benzene is removed from the drying zone through line 3 and admixed with a stream of benzene passing through line 35 to form the net benzene feed stream passed into an alkylation zone 6 via line 5. The benzene is reacted in the alkylation zone with ethylene contained in an ethylene feed stream entering through line 7 to form ethylbenzene. The ethylbenzene, unalkylated benzene and polyalkylated benzenes are removed from the alkylation zone through line 9 as a first effluent stream and passed into a first fractionation zone 10. The polyalkylated benzenes are separated from the effluent and returned to the alkylation zone through line 36. The light gases containing the boron trifluoride circulated through the alkylation zone are also separated in the fractionation zone 10 and recycled to the alkylation zone through line 8.

There is produced in this fractionation zone a first distillate stream comprised of ethylbenzene, which is removed through line 11, and a second distillate stream comprised of benzene which is removed through line 12. The first distillate stream is combined with a recycle ethylbenzene stream passing through line 13 to form the net hydrocarbon feed stream fed to a dehydrogenation zone 14 through line 37. This feed stream is admixed with superheated steam entering through line 30 and passed through dehydrogenation catalyst maintained at an elevated temperature to effect the dehydrogenation of the ethylbenzene and the production of a second effluent stream removed in line 15. This second effluent stream is then cooled by means not shown and combined with an extract stream comprising benzene and water which circulates through line 16.

The second effluent stream is then passed through line 17 into a phase separation zone 18, wherein the condensed water and hydrocarbons separate into two liquid phases. A stream of the hydrocarbon phase is removed through line 19 and passed into a second fractionation zone 20. Distillation conducted within the second fractionation zone separates the incoming hydrocarbon stream into relatively pure streams of ethylbenzene removed in line 13, product styrene removed in line 22 and benzene removed in line 4. The aqueous material which separates out in the liquid phase separation zone 18 is removed as a water stream carried in line 21 and passed into a liquid-liquid extraction zone 27 as the feed stream to this zone.

The second distillate stream removed from the first fractionation zone through line 12 may, according to one embodiment of the invention, be passed in its entirety through line 31 into a water wash zone 23 and therein contacted with clean water which removes a volatile boron-containing complex from the distillate stream. This operation produces a wet benzene stream which is removed in line 24. A first portion of this wet benzene stream is passed through line 26 and charged to the liquid-liquid extraction zone 27 as the solvent stream. Contact of the wet benzene solvent stream with the water stream entering through line 21 results in the transfer of styrene and ethylbenzene from the water stream to the solvent stream. This produces a treated water stream which is removed from the extraction zone through line 28 and passed into a steam generation zone 29. The treated water stream is then converted into the super-heated steam fed to the dehydrogenation zone through line 30. The solvent stream becomes the extract stream which is removed through line 16.

Since all of the wet benzene leaving the water wash zone may not be needed as solvent, a second embodiment of the invention includes the diversion of a second portion of the wet benzene stream through line 25 into the benzene drying zone 2 for recirculation to the alkylation zone. As another alternative, a portion of the second distillate stream passing through line 12 may continue through line 32 and enter a treating zone 33, wherein the boron-containing complex is removed through absorption. This provides a dry and treated benzene stream which is passed through line 34 and admixed with the recycle benzene produced in the second fractionation zone. This benzene is then also recycled to the alkylation zone.

DETAILED DESCRIPTION

Large amounts of styrene are produced annually by the dehydrogenation of ethylbenzene which has been produced by the alkylation of benzene with ethylene. This invention is directed toward an integrated process wherein the alkylation is performed in a reaction zone containing a boron trifluoride promoted catalyst and the ethylbenzene is catalytically dehydrogenated in admixture with steam which is later condensed. The invention comprises a synergistic method of simultaneously alleviating one of the problems associated with each of these operations. Appreciation of the invention therefore requires an initial description of these two operations.

The preferred alkylation process is carried out in the presence of a boron halide and a boron halide modified inorganic oxide, such as alumina, in an anhydrous alkylation promoting environment. However, as a practical matter completely anhydrous streams of charge stock are never available and a minute amount of water inevitably enters the system. It has also been theorized that some water is formed in the reaction zone from free radical hydrogen produced during the reactions. As a result, there is formed in this alkylation reaction environment a reaction product of water and boron halide comprising a relatively non-volatile hydrate of boron oxide, which is normally present in small amounts. (0.02 to about 50 wt. ppm. expressed as elemental boron) in the alkylation zone effluent, typically in a dissolved or suspended state. These hydrates are often referred to simply as borates. This alkylation zone effluent is then passed into a first fractional distillation column from which boron halide vapors are removed overhead, unalkylated aromatic hydrocarbons are removed as a sidecut which is recycled, and alkylated aromatic hydrocarbons are removed as a bottoms stream.

In this first distillation column the relatively non-volatile boron oxide hydrates would ordinarily precipitate out to form insoluble deposits inside the distillation column and the associated reboiler. These deposits gradually accumulate and eventually hamper efficient operation of the column. One method found in the prior art to control the formation of these deposits is to pass a relatively pure boron halide stream into the lower portion of this first distillation column at a point below the level at which the reactor effluent stream passes into the fractional distillation column. This halide then forms a volatile complex with the non-volatile boron oxide hydrates, and the resultant complex is continuously removed from this distillation column as dissolved matter in the unalkylated aromatic hydrocarbon sidecut stream. This stream is also referred to herein as the aromatic hydrocarbon or benzene recycle stream.

In the prior art, the boron oxide hydrate-containing complex in this recycle stream is then removed by passing the benzene stream through beds of alumina absorbent which selectively remove the boron oxide hydrates. However, the use of alumina treaters has several disadvantages. The first is the required periodic replacement of the alumina when the weight percent of boron oxide hydrates reaches a limiting value of about 7–10%. In a large unit, this can lead to relatively large alumina consumption rate. To maintain continuous operation of the process, it is necessary to have two or more alumina treaters which may be used alternately. These treaters and the necessary valving to switch the flow of the benzene sidecut stream between them require a significant capital investment, which is a second disadvantage to the use of alumina treaters. Other disadvantages include the required purging and drying operations before the alumina can be safely removed. The removal and replacement steps require a significant labor force which is expensive and also disruptive to other normal activities. Finally, the spent alumina must be disposed of, and this is presently accomplished only by a landfill operation. The reduction or elimination of these alumina replacement problems and expenses is part of the objective of this invention. It is also the objective of this invention to make more feasible the elimination of the borate removal equipment and to thereby reduce the required capital investment.

The preferred boron halide promoted alkylation process utilizes two reaction zones to produce monoalkylated aromatic hydrocarbons. As used herein, the term "alkylation zone" is intended to include both of these reaction zones. The first reaction zone is used to alkylate the aromatic hydrocarbon feed stream. The second reaction zone is used to transalkylate the polyalkylated aromatics produced in the first reaction zone. The effluent streams of both reaction zones are normally combined and fed directly to a single fractional distillation column, often called the benzene column. The alkylation reaction zone is normally operated in a down flow manner at a temperature of from 100° F. or lower to 600° F. or higher with the preferred operating temperature being from 250° F. to 450° F. The transalkylation reaction zone is normally operated in an upflow manner and maintained at a higher temperature of from 350° F. to 450° F. but could vary in temperature from 200° F. to 700° F. The pressure in the reaction zones may range from atmospheric to 1500 psig. although it is presently desirable to use the pressure range of 300 psig. to 600 psig. The pressure is preferably chosen to be sufficient to maintain the aromatic compounds in a liquid state.

To obtain a high selectivity for the production of a mono-alkylated aromatic hydrocarbon in the alkylation zone, it is best to have present from about 1.5 to about 5 moles of unalkylated aromatic hydrocarbon for every mole of the olefinic compound. This olefinic compound is therefore normally completely reacted in this first reaction zone and is not present in the reactor effluent. To maintain the high excess of aromatic material, it is common practice to recirculate a large amount of unfractionated reactor effluent, which may be up to about 15 times as large as the reactor feed stream or net reactor product. The liquid hourly space velocity may vary between 0.5 and 10. In the transalkylation zone, an excess of unalkylated aromatic hydrocarbons over polyalkylated aromatic hydrocarbons is maintained, with the relative ratio being from about 0.5 to about 3 moles of unalkylated aromatic hydrocarbons per mole of polyalkylated aromatic hydrocarbon. The liquid hourly space velocity of the reactants in the transalkylation zone is from about 0.2 to about 3. Operating conditions in either zone may be varied to correspond to the type of alkylation step to be effected so as to provide optimum yields.

The alkylation reaction, as well as the associated transalkylation reaction, are preferably promoted through the use of a boron halide and a boron halide modified carrier as a catalyst. Preferably, the boron halide is boron trifluoride. The carrier is preferably an inorganic oxide and may be selected from among many inorganic oxides including alumina, silica, boria, oxides of phosphorus, titanium dioxide, zirconium dioxide, chromia, etc., and various naturally occurring inorganic oxides of various states of purity, such as clay or diatomaceous earth. Of the above-mentioned inorganic oxides, the gamma and theta forms of alumina are most readily modified by boron trifluoride and the use of one or both of these is preferred. The modification of the carrier may be carried out prior to or simultaneous with the passage of the reactants over the carrier. Most simply put, this modification is accomplished by the passage of a boron halide-containing gas stream over a bed of the carrier material maintained at an elevated temperature of from about 300° F. to about 500° F. If the modification is carried out simultaneously with the passage of reactants over the carrier, the catalyst will exhibit an induction period during which the alkylation and transalkylation reactions will not take place to any great extent for some hours. To maintain the catalyst in an active state during operation, boron trifluoride is recirculated to each reaction zone at the relatively small rates of about 2000 ppm. in the alkylation zone and about 3500 ppm. in the transalkylation zone.

It is preferred that the reactants charged to the alkylation zone are ethylene and benzene in order to produce ethylbenzene. For this reason, the operation of the invention will be described basically in terms of the alkylation of benzene. However, the invention is not inherently limited to these substances and may be applied to other combination alkylation-dehydrogenation processes utilizing a boron halide promoted catalyst in the alkylation zone. The feed streams to the alkylation zone may be characterized in general as comprising an aromatic hydrocarbon and an olefinic compound. Besides benzene, the aromatic hydrocarbon to be alkylated may be toluene, a xylene, ethylbenzene or isopropylbenzene, etc. or a higher molecular weight hydrocarbon with one or more side chains or rings of from one to ten carbon atoms each. The olefinic compound in the feed stream to the alkylation zone will typically be a rather low molecular weight olefin such as ethylene, propylene or butene. It may however be a polyolefin, acetylenic hydrocarbon, alcohol, ether, ester or other olefin-acting compound or a higher molecular weight olefin, such as octene, or an olefin polymer, such as propylene trimer or propylene tetramer. Cyclo-olefins, such as cyclopentene and methylcyclohexene, and certain olefin-acting substances capable of producing olefinic hydrocarbons or intermediates under the conditions of operation utilized in the process are also suitable. One such grouping includes alkyl halides capable of undergoing dehydrohalogenation to form olefins. Examples of these are ethyl fluoride, isopropyl fluoride, n-propyl chloride, isobutyl bromide, etc.

The effluents of both the first and second reaction zone are combined to form a stream referred to herein as the alkylation zone effluent stream or first effluent stream. This stream is then passed into the first of two fractionation zones used in the combined process. This first fractionation zone preferably comprises two fractionation columns. The first effluent stream is fed into the first of these columns, which is designed and operated so to produce a recycle stream containing most of the unalkylated aromatic hydrocarbon contained in the first effluent stream. This stream is referred to herein as the second distillate stream, and when the aromatic hydrocarbon is benzene, the first column is commonly referred to as the benzene column. The second distillate stream is also referred to as the benzene sidecut stream. To produce a benzene recycle stream, it is normally operated at a bottom pressure of about 15 psig. and with about a 5 psig. pressure drop through the column. The liquid temperature at the bottom of the column will be about 350° F. to ensure removal of the benzene from the alkylated benzenes being withdrawn. The temperature at the point of removal of the benzene sidecut will be about 210° F., and the top of the column will be maintained at about 200° F. The alkylated benzenes are separated in a second fractional distillation column commonly called an ethylbenzene column, which is maintained at about 10 psig. with a bottom temperature of about 425° F. and a top temperature of about 280° F. The monoalkylated benzene is removed as the net overhead product in a stream referred to herein as the first distillate stream.

The boron oxide hydrates formed in the alkylation zone enter the benzene column in the first effluent stream. If left untreated, these non-volatile compounds settle on the internal surfaces of the column and the associated reboiler. This decreases the efficiency of the column and would eventually require the process to be stopped to allow removal of these deposits. These deposits are prevented by charging a stream of a relatively pure boron halide, preferably boron trifluoride when it is used to promote the reaction, into a lower portion of the benzene column. This boron halide stream should enter the column below the point at which the alkylation zone effluent enters the column. The charged boron halide combines with the boron oxide hydrates to form a soluble and volatile complex which ascends the column. This complex has about the same volatility as the benzene, and therefore is removed in the second distillate stream or benzene sidecut. At this point, the prior art has resorted to passing the entire second distillate stream through beds of absorbent alumina. This however has the disadvantages previously pointed out.

The first distillate stream is fed into a catalytic dehydrogenation zone. As this zone will not produce a 100% conversion of the incoming material, a recycle stream of the alkylaromatic hydrocarbon separated in a second distillation zone is combined with the first distillate stream prior to its entrance into the dehydrogenation zone. The dehydrogenation process is endothermic, and therefore the predominant processes for the production of styrene admix sizable amounts of superheated steam with the vaporized ethylbenzene before it is fed into the reaction zone. The superheated steam acts as a heat source which allows a greater amount of dehydrogenation to be performed in the catalyst bed before the temperature becomes too low for the reaction to proceed. The steam also acts as a diluent for the reaction products, which discourages polymerization.

The dehydrogenation zone preferably comprises two or three beds of dehydrogenation catalyst with means for the intermediate addition and admixture of steam. Suitable systems are presented in U.S. Pat. Nos. 3,498,755; 3,515,763; and 3,751,232. The catalyst beds may be contained in separate reaction vessels and may have either a cylindrical or an annular shape. Different catalysts may be used in different beds as described in U.S. Pat. No. 3,223,743. Such catalysts generally consist of one or more metallic components selected from Groups VI and VIII of the periodic table. These metallic components are typically carried on a refractory inorganic oxide material such as alumina, silica, boria or mixtures thereof. One typical catalyst comprises 85% by weight ferric oxide, 2% chromia, 12% potassium hydroxide. A second typical catalyst comprises 90% by weight iron oxide, 4% chromia and 6% potassium carbonate. Methods for preparing suitable catalysts are well known in the art. This is demonstrated by the teachings of U.S. Pat. No. 3,387,052, which describes the manufacture of a catalytic composite of at least 35 wt.% iron oxide as an active catalytic agent, from about 1 to 8 wt.% zinc or copper oxide, about 0.5 to 50 wt.% of an alkali promoter, and from about 1 to 5 wt.% chromic oxide as a stabilizer and a binding agent. Catalysts preferably employed are available commercially and are commonly referred to as "Shell 105" or "Shell 205".

Dehydrogenation conditions in general include a temperature of about 1000° F. to about 1800° F., and preferably about 1050° F. to about 1250° F. The temperature required for any specific unit will depend on the activity of the catalyst employed. The pressure maintained within the dehydrogenation zone is generally quite low and may range from about 0 to 100 psig., with a preferred pressure range being from about 2.0 to 10 psig. The feed stream is charged to the dehydrogenation zone at a liquid hourly space velocity, based on liquid hydrocarbon charge at 60° F., of about 0.1 hr.$^{-1}$ to about 1.0 hr.$^{-1}$, and preferably from 0.2 to 0.7 hr.$^{-1}$.

As previously mentioned, the alkylaromatic to be dehydrogenated is admixed with superheated steam to counteract the temperature lowering effect of the endothermic dehydrogenation reaction. Preferably, the steam is admixed with the feed stream and also added at intermediate points within the reaction zone. However, as an alternative to using steam some processes utilize indirect heat exchange of the reactants or heating elements within the catalyst bed. The steam and alkylaromatic hydrocarbon can be separately heated and then mixed prior to contacting the reactants with the catalyst, or the steam and alkylaromatic can be first commingled and then heated. When ethylbenzene is being dehydrogenated, the space velocity, the rate of steam admixture and the inlet temperature are preferably adjusted to result in the effluent of each catalyst bed having a temperature of about 1100° F. Preferably, steam is admixed with the feed stream to the dehydrogenation zone at a rate of about 0.65 to about 1.0 pound of steam per pound of ethylbenzene. A second portion is added to the effluent of the first catalyst bed at a rate of about 1.0 to about 1.2 pounds of steam per pound of effluent, and a third portion is added to the effluent of the second bed at a rate of about 0.8 to about 1.3 pounds per pound of effluent. These rates are adjusted such that the total effluent stream from the dehydrogenation zone will contain from about 3 to about 6 pounds of steam per pound of styrene.

It is not desirable that these large amounts of water enter the fractionation zone downstream. The most feasible way to remove the water is to condense it. In order to condense out this water at the low pressure of the reaction zone effluent, it is necessary to also condense the heavier hydrocarbons. Therefore, most of the water and the hydrocarbons having six or more carbon atoms are condensed at this point. The substantially condensed effluent stream is then passed into a liquid phase separation zone or settler, wherein it separates into a hydrocarbonaceous phase and an aqueous phase. It is desirable to reuse the water which is separated by recycling the water to a steam generation zone because this reduces the necessity of treating additional make-up water, and it also eliminates the problem of disposal of the condensed hydrocarbon-containing water. As used herein, the term "steam generation zone" is intended to include any zone in which relatively pure water is vaporized by indirect heat exchange for the purpose of generating steam. It may therefore range from a low pressure waste-heat boiler to a high temperature direct-fired boiler.

As a part of the condensation procedure, the effluent stream removed from the dehydrogenation zone is often first heat exchanged for the dual purposes of lowering its temperature to prevent polymerization of the styrene and for the recovery of heat. The effluent stream may be heat exchanged against a make-up stream of steam, a reactant stream of this or another process or used as a heat source for fractionation. Commercially, the effluent stream is often passed through several heat exchangers for the heating of different streams. The reaction zone effluent may also be passed through a quench zone to rapidly cool it and lessen polymerization. The quench zone may be located after a heat exchange means as shown in U.S. Pat. Nos. 3,515,765 and 3,515,766, or the effluent stream may pass directly from the reactor into the quench zone as shown in U.S. Pat. No. 3,515,764. The cooling media fed to the quench zone is preferably liquid water removed from the phase separation zone. This water is not treated in the liquid-liquid extraction zone. Admixture with a hereinafter described extract stream dilutes the effluent and also preferably lowers its temperature. The temperature of the effluent stream is finally lowered sufficiently to cause the condensation of essentially all of the hydrocarbons having 6 or more carbon atoms. Preferably, the effluent stream of the reaction zone is cooled to a temperature at which a liquid phase is formed which contains at least 50 percent of the product material and 90 percent of the water in the effluent stream. When large amounts of heat are recovered from the effluent stream, a trim cooler is normally sufficient to finally cool the effluent stream to the desired temperature of about 100° to 150° F. The temperature used will be the maximum temperature consistent with the condensation of the water at the low pressure at this point.

The effluent stream is then passed into a phase separation zone wherein the effluent divides into a hydrocarbonaceous liquid phase, an aqueous liquid phase and a gaseous phase. There will be some water dissolved in the hydrocarbonaceous phase, which comprises ethylbenzene, styrene, benzene and toluene. There will also be some hydrocarbons dissolved in the aqueous liquid phase. The composition of the gaseous phase will vary with the temperature imposed, but will comprise hydrogen, methane, ethane, ethylene, carbon monoxide, carbon dioxide and other light gases which are formed in the process. The gaseous phase will separate from the liquid phase rather easily and is vented off. The gaseous phase is then often treated to recover heavier hydrocarbons, especially benzene, prior to being removed as the off-gas stream. A suitable treating method is to compress this stream to about 50 psig. and then to cool it to about 100° F. The liquid material in the effluent is passed through a quiescent portion of the phase separation zone and the two resulting liquid phases are separated by decantation. The design and operation of phase separation zones is well understood by those skilled in the art. For instance, U.S. Pat. No. 3,702,346 teaches the beneficial higher selectivity derived in a similar dehydrogenation process by maintaining the product settler at a subatmospheric pressure, preferably in the range of from about 200 mm. Hg to about 600 mm. Hg absolute.

The water which is removed from the separation zone will have dissolved in it a varying amount of the hydrocarbons present in the separator. During the manufacture of styrene, it will therefore contain ethylbenzene, styrene, benzene and toluene and various polymeric compounds normally referred to as tar. It is recognized in the art that the styrene, ethylbenzene and tar must be removed before this water stream can be reused for the generation of steam. If this is not done, these materials will cause a severe coking problem in the tubes of the superheater causing a rapid shut-down of the process. Furthermore, the styrene forms a polystyrene coating on the surface of feed-effluent heat exchanger tubes. This tends to plug the exchanger and to reduce its heat transfer efficiency.

The prior art therefore treats the recycle water stream by first stripping substantially all of the lighter dissolved hydrocarbon materials from the recycle water stream. The stripping of the recycle water stream consumes a fair amount of energy and therefore increases the utility costs of the overall process. The overhead vapor produced by this operation may be condensed and recycled to the phase separation zone. The stripped water is then often passed through a filtration system to remove the remaining hydrocarbons, especially the high-boiling tar which is not removed in the stripping operation. This filtration often comprises the passage of the water stream through a bed of activated charcoal.

It is a part of the objective of this invention to provide a process with reduced utility costs and wherein it is not necessary to strip the recycle water stream. It is a further objective to provide a process wherein portions of the product dissolved in the recycle water stream are removed and recovered in a facile and economic manner.

The present invention resides in part in the realization that the removal of all hydrocarbons from the recycle water stream is not necessary, and that the problems of polymer formation in heat exchangers and coke buildup in boiler tubes can be avoided in a less costly manner by simply displacing undesirable hydrocarbons in an extraction zone instead of removing all hydrocarbons by stripping followed by filtration. It is only necessary to remove the $C_8$-plus alkylaromatic and alkenylaromatic hydrocarbons and tar. Benzene and toluene can link up to form undesired biphenyls but will normally pass through the boiler tubes unaffected. Saturated cyclic compounds, paraffins and olefins will have a minimal detrimental effect as they tend to crack almost completely to methane and hydrogen in the presence of water. Part of the present invention therefore comprises passing the recycle water stream formed by condensing the dehydrogenation zone effluent into a liquid-liquid extraction zone wherein substantially all of the undesired alkylaromatic and alkenylaromatic hydrocarbons are removed from the water stream by contact with a hereinafter described solvent stream comprising hydrocarbons having little or no tendency to obstruct the boiler tubes by coke formation. As used herein, the term "substantially all" refers to a quantity or percentage equal to at least 90% and preferably 95% of the subject material. The concentration of dissolved benzene and toluene in the treated water will be fairly low and can be regulated by adjusting the temperature of the extraction zone.

The solvent stream used in the liquid-liquid extraction zone is formed by water washing the second distillate stream. This is performed to remove the boron-containing complex and comprises contacting and admixing the second distillate stream with a sufficient quantity of water to allow the transfer of substantially all of the boron-containing complex into a separate water phase. The solvent stream therefore has dissolved in it an amount of water which varies according to the temperature imposed during the washing operation. This does not detrimentally affect the operation of the invention as the solvent stream is later used to treat a water stream. It is in fact part of the synergistic combination of the process. The second distillate stream is normally recycled to the alkylation zone. To recycle a wet stream such as produced in the washing operation requires that it be dried to prevent water from entering the reaction zone and forming more borates. The use of the water washing zone by itself is therefore advantageous only if the cost of drying this recycled stream is less than using an absorption zone to remove the boron-containing complex. The invention at least partially removes the necessity of performing this drying by utilizing this wet material as the solvent stream and therefore makes water washing in the alkylation section more economical. At the same time, it provides a desirable solvent stream for use in an extraction zone, which in turn lowers the energy consumption in the dehydrogenation section.

The water washing zone may take on many different forms. One of the simplest would be the injection of a water stream into the transfer line carrying that portion of the stream to be washed. An inline mixer can be placed in this line if the flow is not rapid enough to ensure proper mixing. This zone may also be a separate vessel containing static mixers or mechanical agitators. The zone must function so to cause the intimate contacting of the hydrocarbon stream with water, followed by a phase separation to allow decantation of the two liquids. The amount of water required depends on the operation of the zone and the amount of the complex dissolved in the distillate stream and can be readily calculated by those skilled in the art.

The extract stream removed from the extraction zone will comprise most of the original aromatic solvent, dissolved water and the alkylaromatic and alkenylaromatic hydrocarbons removed from the incoming water stream. As part of the present invention, this stream is used as a substitute for a hydrocarbon slipstream which is often admixed with the effluent stream of the dehydrogenation zone as part of the procedure whereby the effluent stream is cooled and diluted prior to passage into a phase separation zone. This both fulfills the function of the slipstream and provides a use and outlet for the extract stream, which makes the entire process more feasible. It also results in the recycling of the alkylaromatic and alkenylaromatic hydrocarbons from the extraction zone to the phase separation zone, and therefore the recovery of these materials as part of the hydrocarbonaceous phase formed in this zone and passed into the second fractionation zone.

The extract stream may be admixed with the second effluent stream either before or after its insertion into the phase separation zone. It is preferred that the extract stream is admixed with the effluent stream before the phase separation zone, and it is further preferred that it is admixed with the effluent stream before the effluent stream enters the last heat exchanger used in the condensation operation. This eliminates the need to control the diversion of the hydrocarbon slipstream from the hydrocarbon stream sent to the fractionation zone and somewhat simplifies the fabrication and internal structure of the phase separation zone.

Many different mechanical arrangements will perform the function of the liquid-liquid extraction zone, which is to provide the necessary contacting and admixture of the solvent stream and the recycle water stream to cause the transfer of substantially all of the undesirable hydrocarbons into the solvent. It may be a vertical extraction tower as shown in the drawing or a series of batch contacting operations comprised of sequential mixing and settling zones. The extraction tower may use a rotating disk contactor or a pulsed mode of operation to promote extraction. The equipment and design methods needed for the construction and operation of this zone are within the knowledge of those skilled in the art. Detailed information can be obtained from such references as section 14 of the Fourth Edition of *The Chemical Engineers' Handbook*, McGraw-Hill, 1963, or the series of articles on pages 50 to 104 of *Chemical Engineering Progress*, (Vol. 62, No. 9), Sept. 1966. The size of the extraction zone and the required rate of the solvent stream are set by the composition and flow rate of the recycle water stream, the desired composition of the product water stream, the efficiency of the contactor and the solubilities of the various components in the two contacted streams. It is preferred that the extraction zone is operated with countercurrent flow of the solvent and water streams.

As an example, to reduce the styrene concentration of a 380,000 lb/hr water stream from 580 ppm to 5.8 ppm in an extraction zone equivalent to one theoretical stage and operated at 150° F requires a benzene solvent stream of about 21,820 lb/hr. The treated water stream would contain about 379,940 lb/hr of water, 960 lb/hr of benzene and 2 lb/hr of styrene. The exact conditions used in the extraction zone will be set after a consideration of the temperature effect on solubilities, the unadjusted temperature of the chosen input streams and the desired temperatures of the effluent streams. Liquid-liquid extraction zones are normally run in a temperature range of from about 60° F to about 200° F and with a positive pressure ranging from about atmospheric to 200 psig. The extraction zone will often "float" on an upstream or downstream unit to ease pressure regulation problems. The pressure does not affect the extraction operation and is therefore chosen after a consideration of the pressure drop in the extractor, the cost of an extractor designed for a higher pressure and the volatility of the liquids.

From this example it may be seen that the benzene solvent stream required is smaller than the treated water stream. Therefore, even if the extract stream is fractionated to recover the styrene, the utilities cost is reduced due to the smaller amount and the lower latent heat of the benzene stream. The capital costs of using the extraction zone should be no more than using a stripper since the structure of the stripper is very similar to an extraction column, but also includes a reboiler and possibly an overhead condenser. Depending on the ease of the extraction, it may possibly be performed in a number of low cost contacting and settling chambers.

The hydrocarbons condensed from the effluent of the ethylbenzene dehydrogenation zone are separated in a second fractionation zone, such as that described in U.S. Pat. No. 3,525,776. The hydrocarbonaceous phase removed from the phase separation or settling zone is often passed into a first column referred to as a benzene-toluene column. This column is operated at a subatmospheric pressure to allow its operation at lower temperatures and hence reduce the rate of styrene polymerization. Various inhibitors such as elemental sulfur or 2,4-dinitrophenol are added for this same purpose. Sulfur is also introduced into the column by returning high molecular weight material separated from the bottoms stream of a styrene purification column. A more detailed description is contained in U.S. Pat. Nos. 3,476,656; 3,408,263; and 3,398,063. There is effected within the benzene-toluene column a separation of benzene and toluene from the effluent to produce an overhead stream which is substantially free of styrene and ethylbenzene. This stream contains preferably at least 95 mole percent benzene and toluene. It may be further fractionated to produce a substantially pure benzene stream which can then be recycled to the alkylation zone. The bottoms of the benzene-toluene column is passed into a second fractionation column from which ethylbenzene is removed as an overhead product and recycled. The bottoms stream of this column is purified to obtain the styrene. The hydrocarbon stream removed from the phase separation zone may also be fractionated in a different sequence. For instance, the bottoms stream removed from the first column may be a high purity styrene stream and the ethylbenzene may be taken overhead.

In accordance with the above description, the invention may be characterized as a combination process for the manufacture of an alkenylaromatic hydrocarbon by the alkylation of benzene with an olefinic compound and the subsequent catalytic dehydrogenation of a resultant alkylaromatic hydrocarbon which comprises passing a feed stream comprising benzene, the olefinic compound and a boron halide into an alkylation zone maintained at alkylation conditions and effecting the formation of a first effluent stream comprising benzene, the alkylaromatic hydrocarbon and a polyalkylated aromatic hydrocarbon; separating the first effluent stream in a first fractionation zone and effecting the formation of a first distillate stream comprising the alkylaromatic hydrocarbon and a second distillate stream comprising benzene and a volatile complex formed by admixing a boron halide stream charged to the first fractionation zone with boron oxide hydrates contained in the first effluent stream; passing a portion of the second distillate stream into a water wash zone and effecting the removal of the volatile complex from the second distillate stream by contact with water and the formation of a solvent stream comprising benzene and dissolved water; admixing the first distillate stream with superheated steam and passing a resultant admixture into a dehydrogenation zone maintained at dehydrogenation conditions including the presence of a dehydrogenation catalyst, and effecting the formation of a second effluent stream comprising the alkenylaromatic hydrocarbon; condensing hydrocarbons in the second effluent stream having more than five carbon atoms per molecule, and then passing the second effluent stream into a phase separation zone and separating the second effluent stream into an aqueous phase and a hydrocarbon phase comprising the alkenylaromatic hydrocarbon and the alkylaromatic hydrocarbon; removing a liquid hydrocarbon stream from the phase separation zone and passing the liquid hydrocarbon stream into a second fractionation zone, and effecting the formation of a product stream comprising the alkenylaromatic hydrocarbon; removing a water stream comprising the alkenylaromatic hydrocarbon and the alkylaromatic hydrocarbon from the phase separation zone and contacting the water stream with the solvent stream in a liquid-liquid extraction zone, and effecting the transfer of at least a portion of the alkenylaromatic hydrocarbon and the alkylaromatic hydrocarbon in the water stream to the solvent stream and the formation of an extract stream comprising benzene, dissolved water, the alkenylaromatic hydrocarbon and the alkylaromatic hydrocarbon; and admixing the extract stream with the second effluent stream.

The benzene sidecut or second distillate stream will normally be greater in volume than the solvent stream needed to treat the recycle water stream in the extraction zone. The entire stream can still be used as solvent, or one of two alternatives may be employed as the economics of the particular situation dictate. The first alternative is to water wash all of the second distillate stream but to use only a portion of the resultant wet aromatic stream as solvent. The other portion of the wet aromatic stream is then passed into a drying zone and recirculated to the alkylation zone. This drying zone may be any system which economically removes essentially all of the water from this stream. It may therefore comprise suitable vessels filled with a dessicant such as alumina. However, it is preferred that the drying zone comprise a distillation column.

As is well known in the art, a light aromatic feed stream is charged to a drying column near or above its midpoint, and dry benzene is removed from the bottom of the column. To avoid upsetting the operation of the column when large surges of water are present in the feed stream, it is a common practice to charge the feed stream directly to the overhead receiver. When benzene is being dried, the drying column can be effectively operated at a pressure of about 12 psig., a bottom temperature of about 220° F. and a top temperature of about 210° F. During operation, an overhead vapor stream of water and the aromatic hydrocarbon is condensed, and the resulting liquid is collected in an overhead receiver wherein the water and benzene form two distinct phases. The water is removed by decantation and the benzene is returned to the column as reflux, preferably at a temperature close to that of the overhead vapor.

As a second alternative mode of operation, a portion of the second distillate stream is not water washed but is passed through a treating zone to effect the removal of the boron-containing complex. This operation is similar to the prior art and is conducted at ordinary treating conditions. The treating zone may contain any suitable absorbent which selectively removes the complex without contaminating or adversely affecting the aromatic hydrocarbon. It is especially preferred that the treating zone contain alumina.

I claim as my invention:

1. A combination process for the manufacture of an alkenylaromatic hydrocarbon by the alkylation of benzene with an olefinic compound and the subsequent catalytic dehydrogenation of a resultant alkylaromatic hydrocarbon, which comprises:
   a. passing a feed stream comprising benzene, the olefinic compound and a boron trifluoride into an alkylation zone maintained at alkylation conditions and effecting the formation of a first effluent stream comprising benzene, the alkylaromatic hydrocarbon and a polyalkylated aromatic hydrocarbon;

separating the first effluent stream in a first fractionation zone and effecting the formation of a first distillate stream comprising the alkylaromatic hydrocarbon and a second distillate stream comprising benzene and a volatile complex formed by admixing a boron trifluoride stream charged to the first fractionation zone with boron oxide hydrates contained in the first effluent stream;

c. passing at least a portion of the second distillate stream into a water wash zone and effecting the removal of the volatile complex from the second distillate stream by contact with water and the formation of a solvent stream comprising benzene and dissolved water;

d. admixing the first distillate stream with superheated steam and passing a resultant admixture into a dehydrogenation zone maintained at dehydrogenation conditions including the presence of a fixed bed heterogeneous dehydrogenation catalyst, and effecting the formation of a second effluent stream comprising the alkenylaromatic hydrocarbon;
e. condensing hydrocarbons in the second effluent stream having more than five carbon atoms per molecule, and then passing the second effluent stream into a liquid phase separation zone and separating the second effluent stream into an aqueous phase and a liquid hydrocarbon phase comprising the alkenylaromatic hydrocarbon and the alkylaromatic hydrocarbon;
f. removing said liquid hydrocarbon phase from the liquid phase separation zone and passing said liquid hydrocarbon phase into a second fractionation zone, and effecting the formation of a product stream comprising the alkenylaromatic hydrocarbon;
g. removing said aqueous phase comprising the alkenylaromatic hydrocarbon and the alkylaromatic hydrocarbon from the liquid phase separation zone and contacting said aqueous phase with said solvent stream in a liquid-liquid extraction zone, and effecting the transfer of at least a portion of the alkenylaromatic hydrocarbon and the alkylaromatic hydrocarbon in the aqueous phase to said solvent stream and the formation of an extract stream comprising benzene, dissolved water, the alkenylaromatic hydrocarbon and the alkylaromatic hydrocarbon; and,
h. admixing the extract stream with the second effluent stream.

2. The process of claim 1 further characterized in that a second portion of said second distillate stream is passed through a treating zone containing alumina.

3. The process of claim 1 further characterized in that the olefinic compound is an olefin.

4. The process of claim 3 further characterized in that the olefin is ethylene and the alkenylaromatic hydrocarbon is styrene.

* * * * *